US00PP21052P2

(12) United States Plant Patent
Ichie

(10) Patent No.: US PP21,052 P2
(45) Date of Patent: Jun. 8, 2010

(54) ***HYDRANGEA* PLANT NAMED 'DANCING SNOW'**

(50) Latin Name: *Hydrangea macrophylla*
Varietal Denomination: Dancing Snow

(76) Inventor: Toyokazu Ichie, 3-46 Hongou, Kakegawa-city, Shizuoka (JP) 436-0111

( * ) Notice: Subject to any disclaimer, the term of this patent is extended or adjusted under 35 U.S.C. 154(b) by 0 days.

(21) Appl. No.: 12/383,999

(22) Filed: Mar. 31, 2009

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent L Bell
(74) *Attorney, Agent, or Firm*—Penny J. Aguirre

(57) ABSTRACT

A new cultivar of *Hydrangea macrophylla* named 'Dancing Snow' that is characterized by its early spring blooming habit, its ability to re-bloom on new growth after deadheading into fall, its lacecap type inflorescences comprised of a ring of large double white flowers emerging from the central mass of smaller double white flowers, its flowers that are resistant to sun scorch, its compact growth habit, and its hardiness at least to U.S.D.A. Zones 5 to 9.

2 Drawing Sheets

Botanical classification: *Hydrangea macrophylla.*
Varietal denomination: 'Dancing Snow'.

BACKGROUND OF THE INVENTION

The present invention relates to a new and distinct cultivar of *Hydrangea macrophylla* and will be referred to hereafter by its cultivar name, 'Dancing Snow'. 'Dancing Snow' represents a new bigleaf hydrangea, a deciduous shrub grown for landscape use and for use as a potted plant.

'Dancing Snow' was derived from an ongoing controlled breeding program in a nursery that focuses on developing new cultivars of bigleaf hydrangea for container and landscape use. 'Dancing Snow' originated from a cross made in the Inventor's nursery in July 2003 between two unpatented proprietary selections of *Hydrangea macrophylla*; the female parent designated as 00-2A and the male parent designated as 98-50c. The new *Hydrangea* was selected as a unique single plant from the progeny of the cross in June 2006.

Asexual reproduction of the new cultivar was first accomplished by the Inventor using softwood stem cuttings in Shizuoka, Japan in July 2007. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Dancing Snow' as a unique cultivar of *Hydrangea macrophylla.*

1. 'Dancing Snow' is a very early spring bloomer and removal of spent blooms results in repeat bloom from spring into fall in Shizuoka, Japan, Niagara on the Lake, Ontario, Canada, and Warsaw, N.C.
2. 'Dancing Snow' exhibits lacecap type inflorescences comprised of a ring of large double sterile flowers emerging from the central mass of smaller double sterile flowers.
3. 'Dancing Snow' exhibits white flowers that are resistant to sun scorch.

4. 'Dancing Snow' exhibits a compact plant habit with a mature plant size in the landscape of about 92 cm (3 feet) in height and width.
5. 'Dancing Snow' is hardy at least in U.S.D.A. Zones 5 to 9.

'Dancing Snow' differs from its female parent, 00-2A, in having double white flowers whereas 00-2A has single flowers that are light purple in color. 'Dancing Snow' differs from its male parent, 98-50c, in having double white flowers whereas 98-50c has single flowers that are magenta in color. 'Dancing Snow' can also be compared to the cultivar 'Jogasaki' (not patented). 'Jogasaki' differs from 'Dancing Snow' in having double flowers that are pink in color. 'Dancing Snow' is also unique from most lacecap type *Hydrangea* in having double flowers in the center of the inflorescence rather than fertile flowers.

BRIEF DESCRIPTION OF THE DRAWINGS

The accompanying colored photographs illustrate the overall appearance and distinct characteristics of the new *Hydrangea.*

The photographs were taken of a three year-old plant of 'Dancing Snow' as grown outdoors in a 3-gallon container in Shizuoka, Japan.

Figure 1:
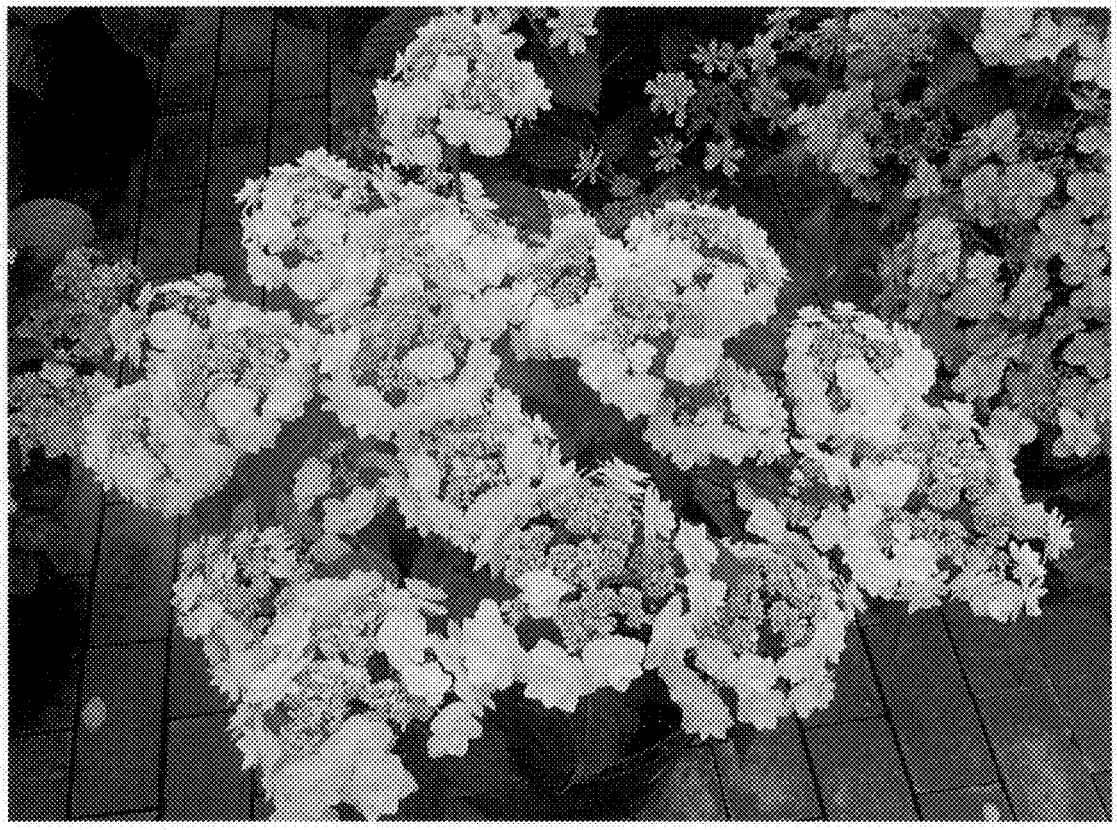

The photograph in FIG. 1 provides a top view of 'Dancing Snow' and illustrates its overall plant habit and blooming habit.

Figure 2:
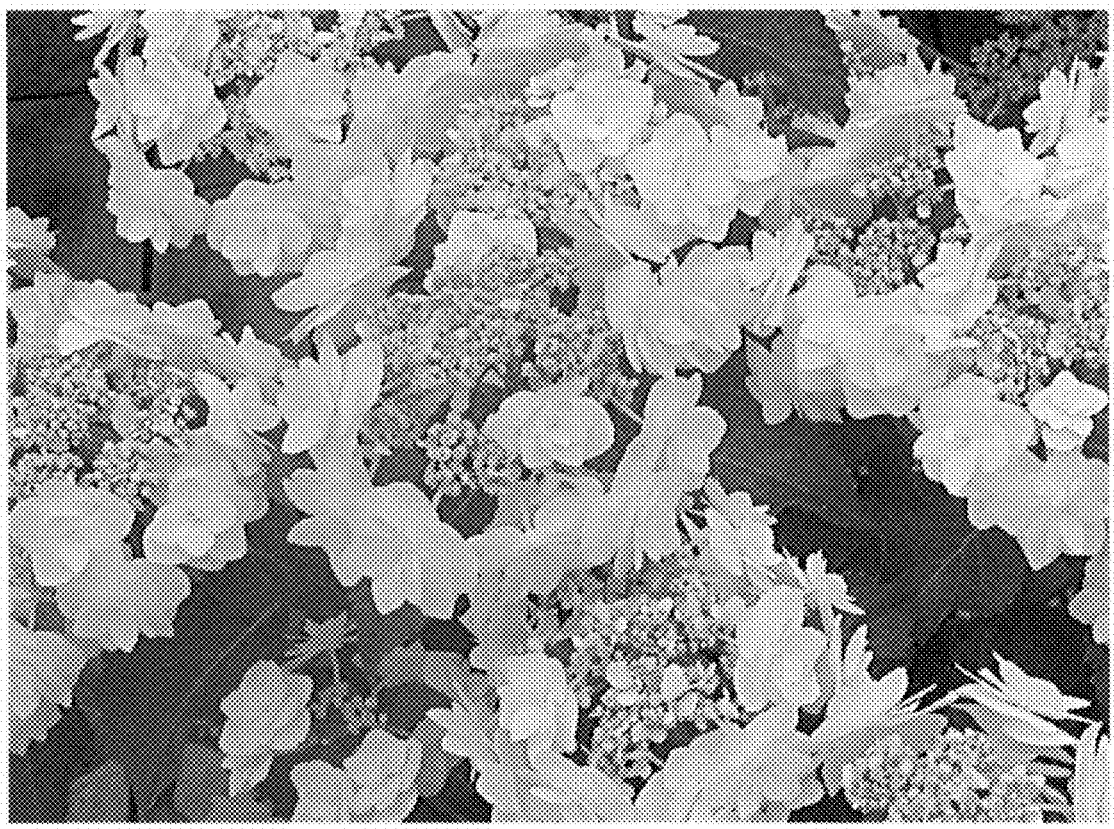

The photograph in FIG. 2 provides a close-up view of the fully open inflorescence.

The colors in the photographs may differ slightly from the color values cited in the detailed botanical description, which accurately describe the colors of the new *Hydrangea.*

BOTANICAL DESCRIPTION OF THE PLANT

The following is a detailed description of three year-old plants of 'Dancing Snow' as grown outdoors in 3-gallon containers in Shizuoka, Japan. Phenotypic differences may be observed with variations in environmental, climatic, and cultural conditions. The color determination is in accordance with the 2007 R.H.S. Colour Chart of The Royal Horticultural Society, London, England, except where general color terms of ordinary dictionary significance are used.

General description:

*Blooming period.*—Very early blooming, removal of spent blooms results in repeat bloom from Spring until fall in Shizuoka, Japan.

*Plant habit.*—Broadly upright, compact, deciduous shrub.

*Height and spread.*—Reaches about 92 cm in height and width when mature in the landscape.

*Hardiness.*—At least to U.S.D.A. Zones 5 to 9.

*Culture.*—Grows best in moist but well-drained, humus-rich soil in full sun or partial shade, has shown good resistance to sun scorch.

*Diseases resistance.*—No susceptibility or resistance to diseases has been observed.

*Root description.*—Fine.

Growth and propagation:

*Propagation.*—Softwood stem cuttings.

*Growth rate and vigor.*—Moderate.

Stem description:

*Stem shape.*—Round, solid.

*Stem strength.*—Strong.

*Stem color.*—New growth; 144B with lenticels 175A and at petiole attachment, woody; blend of 164D and N199C.

*Stem size.*—An average of 21 cm (to base of inflorescence in 3 gallon container), an average of 8 mm in width.

*Stem surface.*—Glabrous, slightly satiny, with about 10 lenticels per 1 sq cm that are up to 1 mm in length and 0.7 mm in width, stem becomes bark-like as it matures.

*Internode length.*—Average of 4.5 cm.

*Branching.*—Lateral branching is determined by pinching; 2 stems develop per pinched node.

Foliage description:

*Leaf shape.*—Ovate.

*Leaf arrangement.*—Opposite.

*Leaf division.*—Simple.

*Leaf number.*—Average of 8 (4 pairs) per lateral branch.

*Leaf base.*—Cuneate.

*Leaf apex.*—Cuspidate.

*Leaf margins.*—Serrated, average of 28 per side on a leaf 14 cm in length.

*Leaf venation.*—Odd-pinnate, recessed on upper surface and raised on lower surface, mid rib color 145C on upper surface and a blend of 144B and 138B on lower surface, all other veins 138A to 138B.

*Leaf size.*—Up to 14 cm in length and 10.5 cm in width.

*Leaf attachment.*—Petiolate.

*Leaf surface.*—Glabrous and dull on upper surface and finely puberulent on lower surface.

*Leaf color.*—Upper surface; 137A, lower surface; 138B.

*Petioles.*—Average of 3 cm in length and 4 mm in width, 144A to 144B in color, glabrous surface.

Inflorescence description:

*Inflorescence type.*—Terminal compound corymb, lacecap form comprised of double large sterile flowers emerging on the perimeter from a mass of smaller double sterile flowers in the center, the eye on many of the flowers is comprised of poorly developed reproductive organs.

*Lastingness of inflorescence.*—Persistent but color is retained for about 4 weeks.

*Inflorescence number.*—One per lateral or sublateral stem if pinched.

*Inflorescence size.*—Ranges from 11 cm in diameter and 5 cm in depth to 17 cm in diameter and 11 cm in depth.

*Flower number.*—About 600 flowers per inflorescence 13 cm in diameter and 7 cm in depth.

*Flower fragrance.*—None.

*Flower aspect.*—Upright with larger perimeter flowers nodding on longer petioles.

*Flower size.*—Perimeter flowers; average of 3.2 cm in diameter and 8 mm in depth, lateral flowers; average of 2.2 mm in diameter and 5 mm in depth, flowers at base of corymbs; 1.3 cm in diameter and 3.5 mm in depth.

*Flower buds.*—Average of 4 mm in length and 3 mm in width, oblong in shape, NN155B in color prior to opening.

*Peduncles.*—For each complex corymb in inflorescence; average of 3.5 cm in length and 4 mm in width, 149D in color, glabrous surface, for individual corymbs; an average of 5 mm in length and 2 mm in width, 149D in color, glabrous surface, peduncle leaves; an average of 2 per corymb, average to 3 cm in length and 1.3 cm in width, oblanceolate in shape, same coloration and surface as stem leaves.

*Pedicels.*—An average of 2 cm in length and 1.5 mm in width and nodding downwards on perimeter flowers, an average of 3 mm in length and 1 mm in width on central flowers (appearing sessile), NN155B in color on perimeter flowers and 144D in color on central flowers, surface glabrous on all flowers.

*Sepals.*—An average of 16 on larger perimeter flowers, average of 12 on smaller central flowers, overlapping and alternately arranged in about 5 rows, rotate and spreading in arrangement, outer tepals are orbicular in shape, inner tepals are ovate to elliptic in shape, entire margin, broadly acute to rounded apex, cuneate to rounded base, size on perimeter flowers; outer tepals an average of 1.8 cm in length and width becoming smaller with each row with inner tepals on average of 6 mm in length and 4 mm in width, size on smaller central flowers is highly variable with some remaining unopened, surface is glabrous and dull on both surfaces, color of upper and lower surface on open flower is N155C, with some speckling on 144A on smaller more basal flowers, color turns to 144C to 144D with outer tepals turning first.

*Eye spot.*—Small and highly variable in color due the presence of variable and poorly developed reproductive organs; 144D to NN155C to 165C.

Reproductive organs: On most flowers the eye is comprised of poorly developed reproductive organs, primarily pistils and stamens were not identifiable. When distinguishable, pistils are club shaped, translucent to 144D in color with apex 200A in color.

It is claimed:

1. A new and distinct cultivar of *Hydrangea* plant named 'Dancing Snow' substantially as herein illustrated and described.

* * * * *